US011304687B2

(12) United States Patent
Baril et al.

(10) Patent No.: US 11,304,687 B2
(45) Date of Patent: Apr. 19, 2022

(54) TISSUE SPECIMEN BAG FURLING DEVICE AND METHOD (71) Applicant: COVIDIEN LP, Mansfield, MA (US)

(72) Inventors: Jacob C. Baril, Norwalk, CT (US); Saumya Banerjee, Hamden, CT (US); George S. Matta, Plainville, MA (US); Matthew A. Dinino, Newington, CT (US); Justin J. Thomas, New Haven, CT (US); Roy J. Pilletere, North Haven, CT (US)

(73) Assignee: Covidien LP, Mansfield, MA (US)

(*) Notice: Subject to any disclaimer, the term of this patent is extended or adjusted under 35 U.S.C. 154(b) by 302 days.

(21) Appl. No.: 16/539,198

(22) Filed: Aug. 13, 2019

(65) Prior Publication Data
US 2021/0045725 A1 Feb. 18, 2021

(51) Int. Cl.
A61B 17/00 (2006.01)

(52) U.S. Cl.
CPC ............ A61B 17/00234 (2013.01); A61B 2017/00287 (2013.01); A61B 2017/00367 (2013.01); A61B 2017/00407 (2013.01)

(58) Field of Classification Search
CPC .... A61B 17/00234; A61B 2017/00287; A61B 2017/00367; A61B 2017/00407; A61B 2017/00867; A61B 2017/00991; A61B 17/2841; A61B 17/2909
See application file for complete search history.

(56) References Cited

U.S. PATENT DOCUMENTS

| 5,788,709 | A | 8/1998 | Riek et al. |
| 6,059,793 | A | 5/2000 | Pagedas |
| 6,156,055 | A | 12/2000 | Ravenscroft |
| 6,162,209 | A | 12/2000 | Gobron et al. |
| 6,171,317 | B1 | 1/2001 | Jackson et al. |
| 6,206,889 | B1 | 3/2001 | Bennardo |
| 6,224,612 | B1 | 5/2001 | Bates et al. |
| 6,228,095 | B1 | 5/2001 | Dennis |
| 6,248,113 | B1 | 6/2001 | Fina |
| 6,258,102 | B1 | 7/2001 | Pagedas |
| 6,264,663 | B1 | 7/2001 | Cano |
| 6,270,505 | B1 | 8/2001 | Yoshida et al. |
| 6,280,451 | B1 | 8/2001 | Bates et al. |
| 6,344,026 | B1 | 2/2002 | Burbank et al. |
| 6,350,266 | B1 | 2/2002 | White et al. |

(Continued)

Primary Examiner — Kathleen S Holwerda
Assistant Examiner — Brooke N Labranche
(74) Attorney, Agent, or Firm — Carter, DeLuca & Farrell LLP (57) ABSTRACT A device for furling a tissue specimen retrieval bag includes a housing supporting a spindle assembly therein, the spindle assembly including a drive shaft having a proximal end, a distal end, and a gear disposed therebetween. An activation switch is pivotably coupled to the housing and is configured for selective, operable engagement with the gear. The activation switch is selectively positionable relative to the gear between a first position wherein the gear and drive shaft are locked from rotation in a first direction and a second position wherein the gear and drive shaft are free to rotate in the first direction. An elongated shaft is operably coupled to the distal end of the drive shaft and is configured for rotation therewith. A biasing element is configured to provide a rotational load to the drive shaft.

16 Claims, 8 Drawing Sheets

(56) References Cited

U.S. PATENT DOCUMENTS

| | | |
|---|---|---|
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2013/0103042 A1* | 4/2013 | Davis ............... A61B 17/00234 606/114 |
| 2015/0209021 A1 | 7/2015 | Davis |
| 2018/0199961 A1 | 7/2018 | Prior et al. |

\* cited by examiner

TISSUE SPECIMEN BAG FURLING DEVICE AND METHOD

BACKGROUND

Technical Field

The present disclosure relates to tissue specimen retrieval from an internal body cavity and, more particularly, to instruments utilized with tissue specimen retrieval devices that facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment such as a specimen retrieval bag is highly desirable to inhibit seeding of cancer cells. Thus, with respect to breaking down large tissue specimens for retrieval through minimally-invasive openings, there is the added challenge of doing so within an enclosed environment.

Various specimen retrieval devices are known and are configured for utilization with the deployment and retrieval of the tissue specimen and the specimen retrieval bag. Typically the end effector assembly of the specimen retrieval device cooperates with the specimen retrieval bag. The specimen retrieval bag typically includes a bag brim having a flexible wire support that is transitionable from a first collapsed configuration to a second expanded configuration for encapsulating tissue specimens. Flexible Nitinol®, one or more torsion springs or the like are routinely utilized to accomplish the transition.

The specimen retrieval bag is typically stored in a furled configuration to facilitate loading onto an tissue retrieval device or to facilitate insertion into an incision or natural body orifice. Furling the tissue specimen bag prior to loading or insertion tends to be difficult during operating conditions.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

In accordance with aspects of the present disclosure is a device for furling a tissue specimen retrieval bag that includes a housing supporting a spindle assembly therein, the spindle assembly including a drive shaft having a proximal end, a distal end, and a gear disposed therebetween. An activation switch is pivotably coupled to the housing and is configured for selective, operable engagement with the gear. The activation switch is selectively positionable relative to the gear between a first position wherein the gear and drive shaft are locked from rotation in a first direction and a second position wherein the gear and drive shaft are free to rotate in the first direction. An elongated shaft is operably coupled to the distal end of the drive shaft and is configured for rotation therewith. A biasing element is configured to provide a rotational load to the drive shaft.

In aspects according to the present disclosure, the biasing element is a constant force spring, a torsion spring, a compression spring, or an extension spring. In other aspects according to the present disclosure, the biasing element is selectively loadable by rotating the distal end of the drive shaft in a second direction, opposite the first direction. In still other aspects according to the present disclosure, the activation switch includes a pawl-like proximal end that is configured to selectively engage the gear and allow rotation of the gear and drive shaft in the second direction and prevent rotation of the gear and drive shaft in the first direction In aspects according to the present disclosure, the activation switch is biased in the first position to facilitate loading the drive shaft. In other aspects according to the present disclosure, the distal end of the spindle assembly includes a ratchet-like mechanism to facilitate loading the drive shaft.

In accordance with additional aspects of the present disclosure is a device for furling a tissue specimen retrieval bag that includes a housing supporting a spindle assembly therein. An activation switch is pivotably coupled to the housing and is configured for selective, operable engagement with the gear. The activation switch is selectively positionable relative to the gear between a first position wherein the gear and drive shaft are locked from rotation in a first direction and a second position wherein the gear and drive shaft are free to rotate in the first direction. An elongated shaft is operably coupled to the distal end of the drive shaft and is configured for rotation therewith, the elongated shaft including a slot defined therein and configured to operably engage a dowel pin associated with the tissue specimen bag for loading the tissue specimen bag atop the elongated shaft. A biasing element is configured to provide a rotational load to the drive shaft, wherein, once the dowel pin is operably engaged within the slot of the elongated shaft, actuation of the activation switch to the second position rotates the drive shaft and the elongated shaft to furl the tissue specimen bag about the elongated shaft.

In aspects according to the present disclosure, the dowel pin slidingly engages the elongated shaft. In other aspects according to the present disclosure, the biasing element is a constant force spring, a torsion spring, a compression spring, or an extension spring. In still other aspects according to the present disclosure, the biasing element is selectively loadable by rotating the distal end of the drive shaft in a second direction, opposite the first direction.

In still other aspects according to the present disclosure, the activation switch includes a pawl-like proximal end that is configured to selectively engage the gear and allow rotation of the gear and drive shaft in the second direction and prevent rotation of the gear and drive shaft in the first direction. In yet other aspects according to the present disclosure, the activation switch is biased in the first position to facilitate loading the drive shaft.

In aspects according to the present disclosure, the distal end of the spindle assembly includes a ratchet-like mechanism to facilitate loading the drive shaft. In other aspects according to the present disclosure, the dowel pin is welded, glued, molded or integrated onto an outer periphery of the tissue specimen bag.

In accordance with additional aspects of the present disclosure, a method of furling a tissue specimen bag includes loading a tissue specimen bag onto an elongated shaft of a tissue furler, the tissue furler including: a housing supporting a spindle assembly therein, the spindle assembly including a drive shaft having a gear disposed therebetween, the elongated shaft operably coupled to a distal end of the drive shaft for rotation therewith; an activation switch pivotably coupled to the housing and configured for selective, operable engagement with the gear, the activation switch selectively positionable relative to the gear between a first position wherein the gear and drive shaft are locked from rotation in a first direction and a second position wherein the gear and drive shaft are free to rotate in the first direction; and a biasing element configured to provide a rotational load to the drive shaft.

The method further includes actuating the activation switch to rotate the drive shaft and the elongated shaft to furl the tissue specimen bag about the elongated shaft.

In aspects according to the present disclosure, prior to loading the tissue specimen bag onto the elongated shaft, the method further includes rotating the distal end of the drive shaft in a second direction, opposite the first direction, to the load the biasing element.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Turning to FIGS. 1-6, a tissue specimen bag furler provided in accordance with the present disclosure is shown generally identified by reference numeral 10 (hereinafter "furler 10"). Furler 10 includes an outer housing 20 including proximal and distal ends 22 and 24, respectively, with a grip portion 25 disposed therebetween. Distal end 24 is configured to operably couple to a proximal end 14 of an elongated shaft 12 that extends therefrom. A distal end 16 of the elongated shaft 12 is configured to operably couple to a mechanical interface, e.g., dowel pin 68, disposed on a tissue specimen retrieval bag 60 (hereinafter "bag 60") as explained in further detail below (See FIGS. 2A and 2B). Elongated shaft 12 includes a slot 17 defined therein and extending at least partially therealong configured to slidingly receive the dowel pin 68 during operable engagement of the furler 10 with the bag 60 as explained in more detail below with reference the operation of the furler 10 (See FIG. 1B).

Figure 1A:
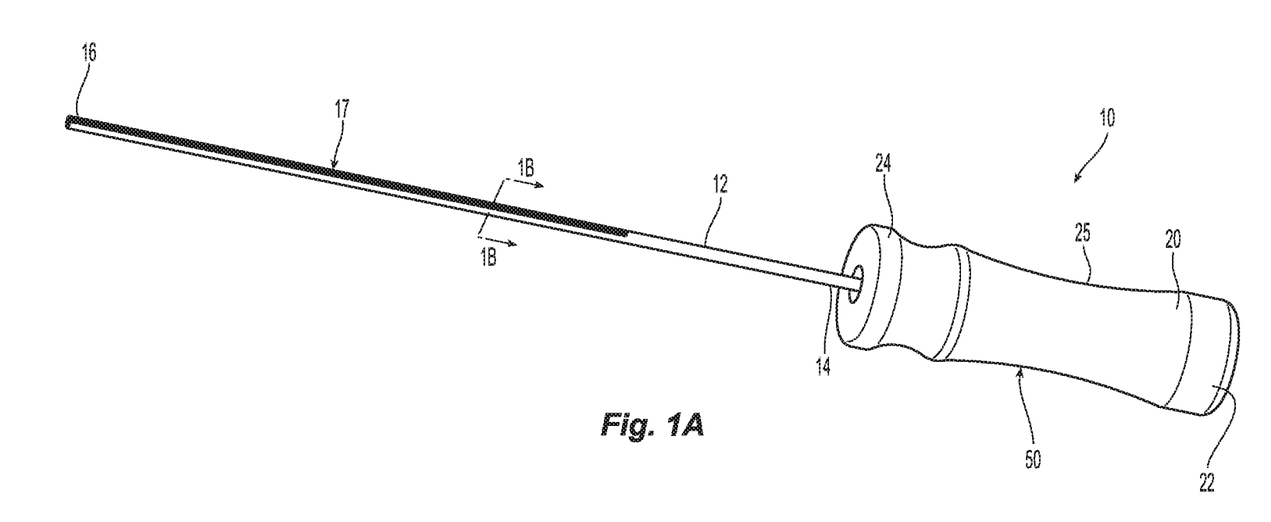
FIG. 1A is a perspective view of a tissue specimen bag furler provided in accordance with aspects of the present disclosure.
Figure 1B:
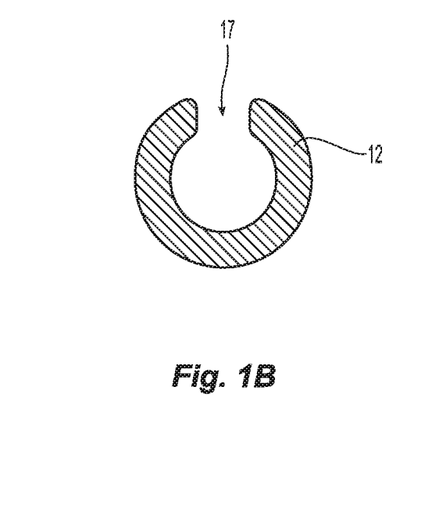
FIG. 1B is a cross sectional view of the area of detail of FIG. 1A.
Figure 2A:
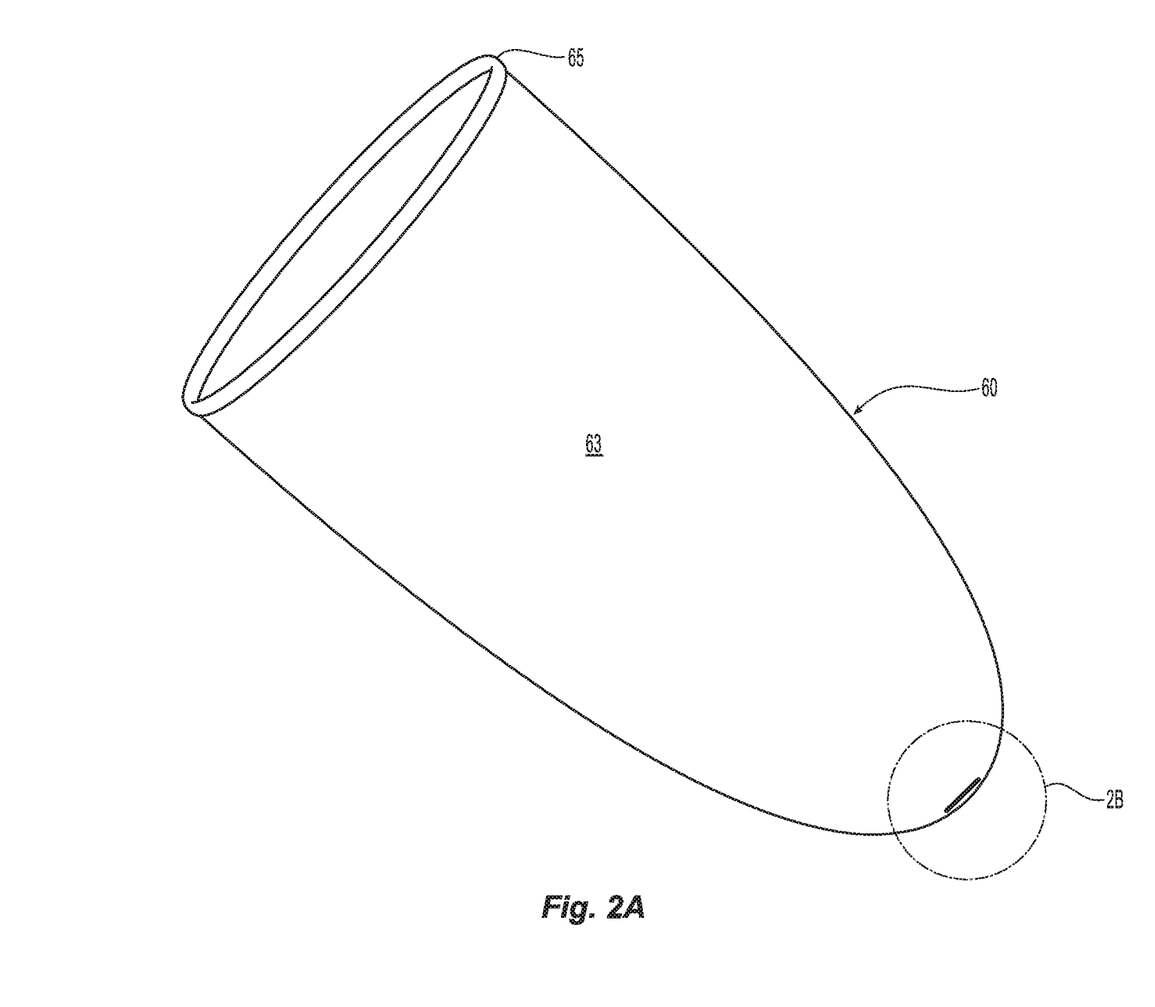
FIG. 2A is a perspective view of the tissue specimen retrieval bag for use with the tissue specimen bag furler of FIG. 1, the tissue specimen retrieval bag shown in an unfurled configuration.
Figure 2B:
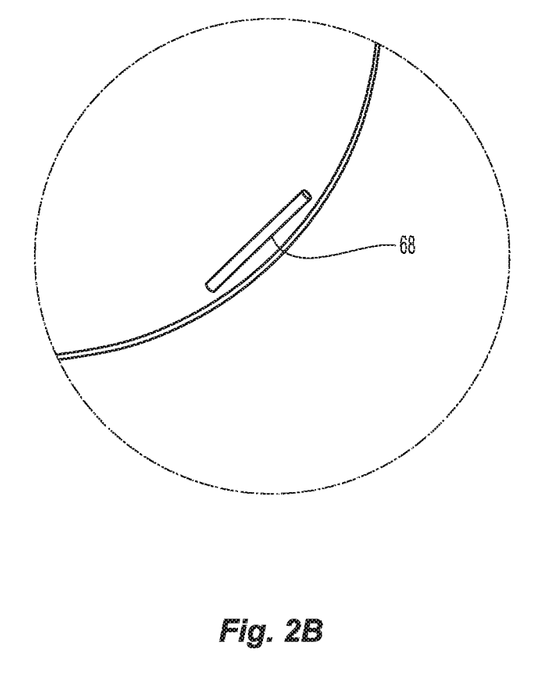
FIG. 2B is a greatly enlarged view of a dowel pin configured to selectively couple to the tissue specimen bag furler to facilitate furling the tissue specimen retrieval.

Bag 60 includes an outer bag rim 65 that is configured to support bag 60 in such a fashion as to define an enclosure 63 when the bag 60 is unfurled. Enclosure 63 is of sufficient dimension to receive one or more tissue specimens when samples during a particular surgical procedure.

Bag rim 65 is configured to be flexible such that the bag 60 and bag brim 65 are easily transitionable between a first collapsed configuration when the bag 60 is furled (as explained below) and a second expanded configuration once the bag 60 is unfurled. As such, bag brim 65 may be made from any flexible material that is easily expandable from a collapsed configuration to unfurl bag 60. Bag 60 may include any suitable rollable material such as nylon, polyurethane, etc., and may be configured to selectively attach and/or be removed from and end effector (not shown) of a specimen retrieval device (not shown).

As mentioned above and as shown in FIGS. 2B, 4A, and 4B bag 60 includes a mechanical interface, e.g., dowel pin 68, that is operably associated with the bottom portion of the bag 60 on an outer surface thereof. Dowel pin 68 is configured to project from the outer surface of bag 60 to engage the distal end of shaft 12 within elongated slot 17. Dowel pin 68 may be welded, glued, molded or integrated onto the outer periphery of the bag 60 in any way known in the art. Once engaged, the bag 60 and the dowel pin 68 are slid along slot 17 of shaft 12 in the direction of arrow "S" such that the entirety of the bag 60 is positioned adjacent the shaft 12. Once positioned, the furler 10 may be selectively activated to rotate the shaft 12 in the direction "R" to furl the bag 60 and collapse the rim 65 (See FIG. 4B). Details relating to the operation of the furler 10 are explained in further detail below with reference to FIGS. 3, 5A and 5B.

Figure 3:
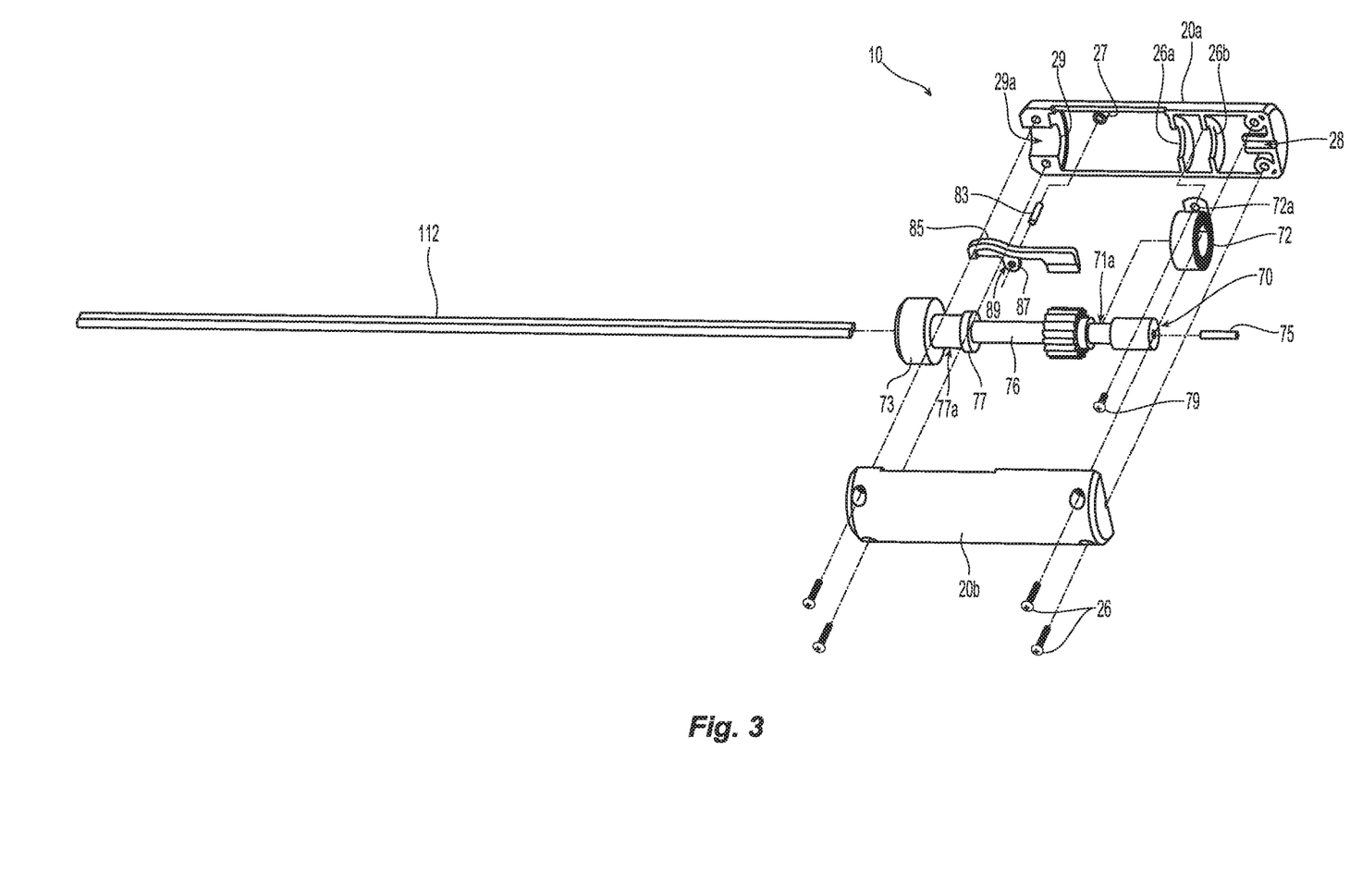
FIG. 3 is an exploded, perspective view of the tissue specimen bag furler.
Figures 4A, 4B:
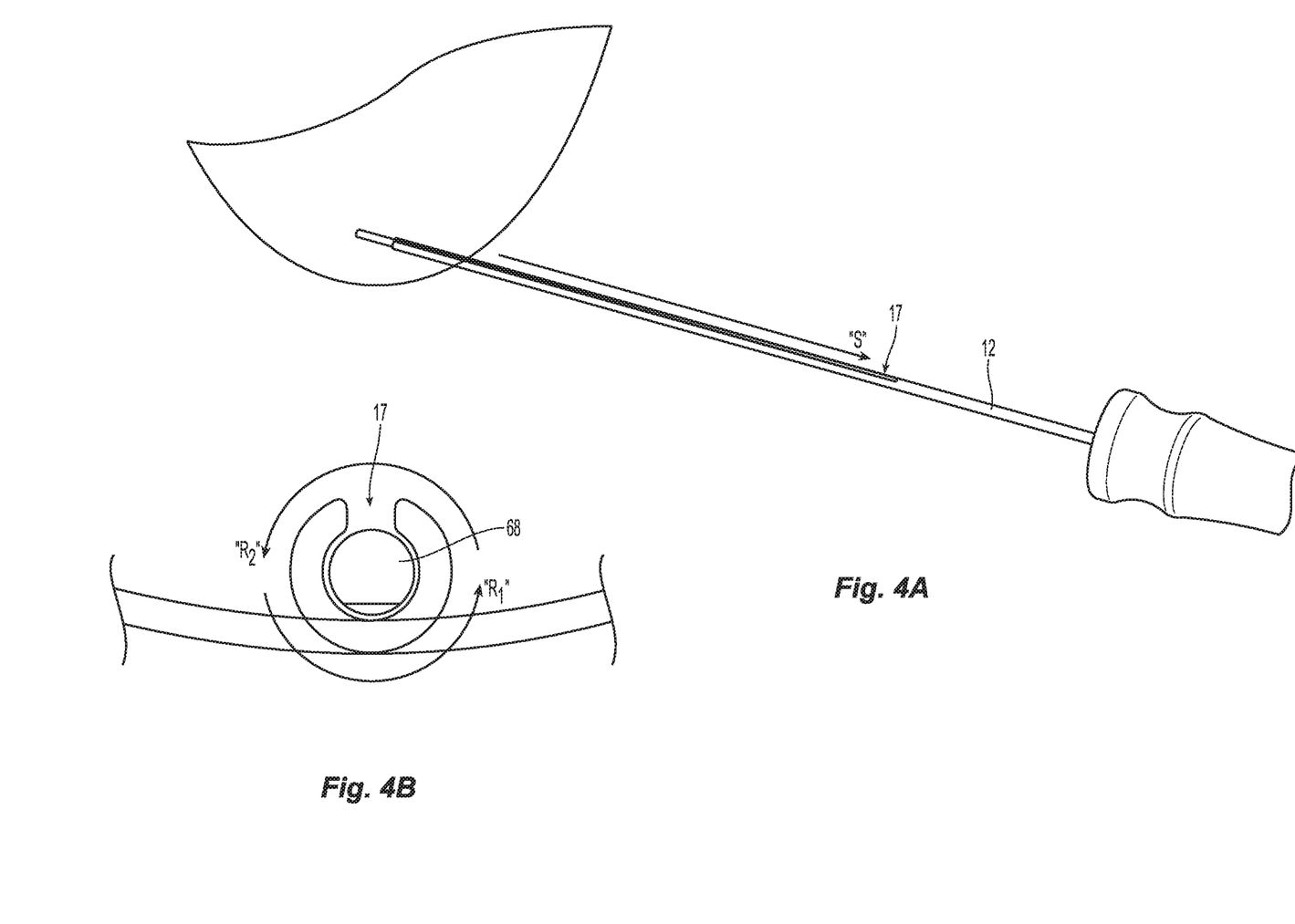
FIG. 4A is a perspective view showing the engagement of the dowel pin with a shaft of the tissue specimen bag furler.
FIG. 4B is a cross sectional view showing the dowel pin engaged with the shaft of the tissue specimen bag furler poised for rotation to furl the tissue specimen bag in the direction denoted by the arrow.

FIG. 3 shows an exploded view of the furler 10 and the various internal components therein. More particularly, furler 10 includes housing halves 20a and 20b that combine to form housing 20. Halves 20a and 20b may be ultrasonically welded together or screwed together via a series of screws 26.

A drive spindle assembly 70 (hereinafter "spindle assembly 70") is encapsulated by housing 20 and is configured to selectively rotate the shaft 12 upon activation thereof. More particularly, spindle assembly 70 includes a drive shaft 76 having proximal and distal ends, 71 and 73, respectively. Spindle assembly 70 is supported on a pin 75 disposed at the proximal end thereof that operably engages a corresponding support 28 disposed within housing halves 20a, 20b (the support 28 in housing half 20b is not shown). Spindle assembly 70 is configured to support a gear 74 for rotation thereon and that operably couples to an activation switch 85 as explained in more detail below. Drive shaft 76 includes a recess 71a defined near the proximal end 71 thereof that is configured to support a spring 72 thereon. Spring 72 may be any type of drive spring, e.g., a constant force spring, torsion spring, leaf spring, coil spring, etc. For the purposes herein, a constant force spring 72 (hereafter "CFS 72") is described.

CFS 72 is supported near the proximal end 71 of the drive shaft 12 and seats between a pair of flanges 26a and 26b disposed within the housing half 20a. Similar flanges (not shown) are disposed within housing half 20b and together with flanges 26a, 26b cooperate to encapsulate the CFS 72 when the housing 20 is assembled. CFS 72 engages shaft 12 in a friction-fit manner such that rotation of the CFS 72 correspondingly rotates the shaft 12 and the gear 74. CFS 72 may be installed under a bias or selectively loaded as explained below. A distal portion 72a of the CFS 72 is anchored to the housing half 20a.

Activation switch 85 includes a pivot flange 87 that is supported between housing halves 20a, 20b via a pivot pin 83 which is, in turn, support on either end by pivot supports 27 (pivot support 27 is not shown on housing half 20b). Pivot flange 87 includes a pivot hole defined therethrough for engaging pivot pin 83. When housing 20 is assembled, activation switch 85 is disposed in a normally horizontal configuration relative to housing 20. When assembled, a proximal end 85b of activation switch 85 engages gear 74 to prevent rotation thereof which, in turn, prevents CFS 72 from rotating shaft 12. Activation switch 85 may be biased in the normally horizontal and locked configuration.

The CFS 72 may be preloaded for single or multiple use or loadable via one or more loading features or techniques. Various loading features are envisioned. For example, the distal end 73 of the drive shaft 76 may include a mechanical interface 73a that is configured to engage the shaft 12. One of more rotary gears (not shown) may be utilized for this purpose and act as mechanical interface 73a for engaging shaft 12 (as explained below with reference to FIG. 6). Rotation of the gear 74 correspondingly rotates the mechanical interface 73a such that, upon activation of the activation switch 85, shaft 12 is rotated.

Figure 5A:
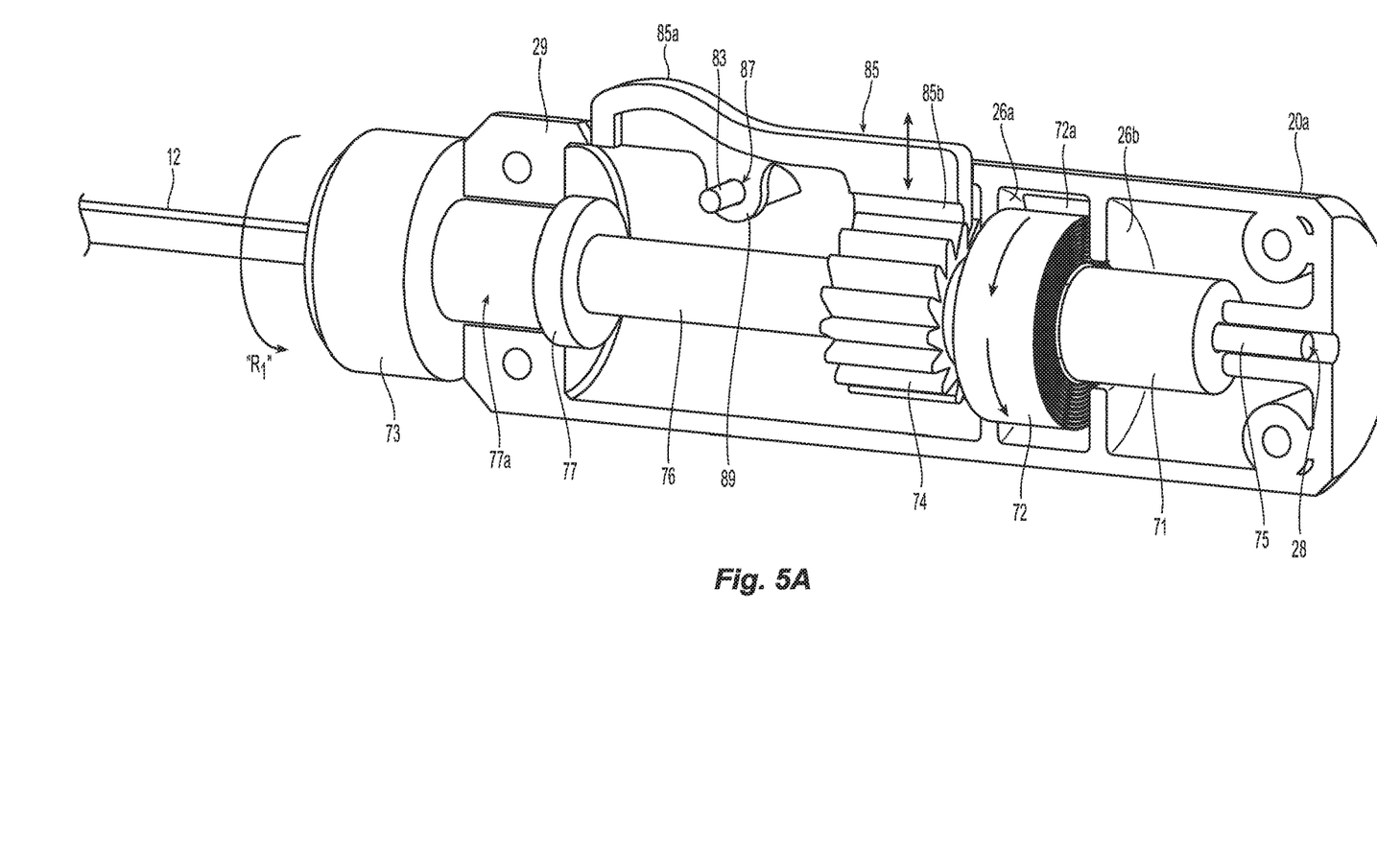
FIG. 5A is an interior, perspective view of the tissue specimen bag furler showing the various components disposed therein and showing the tissue specimen bag furler in a locked orientation prior to activation.
Figure 5B:
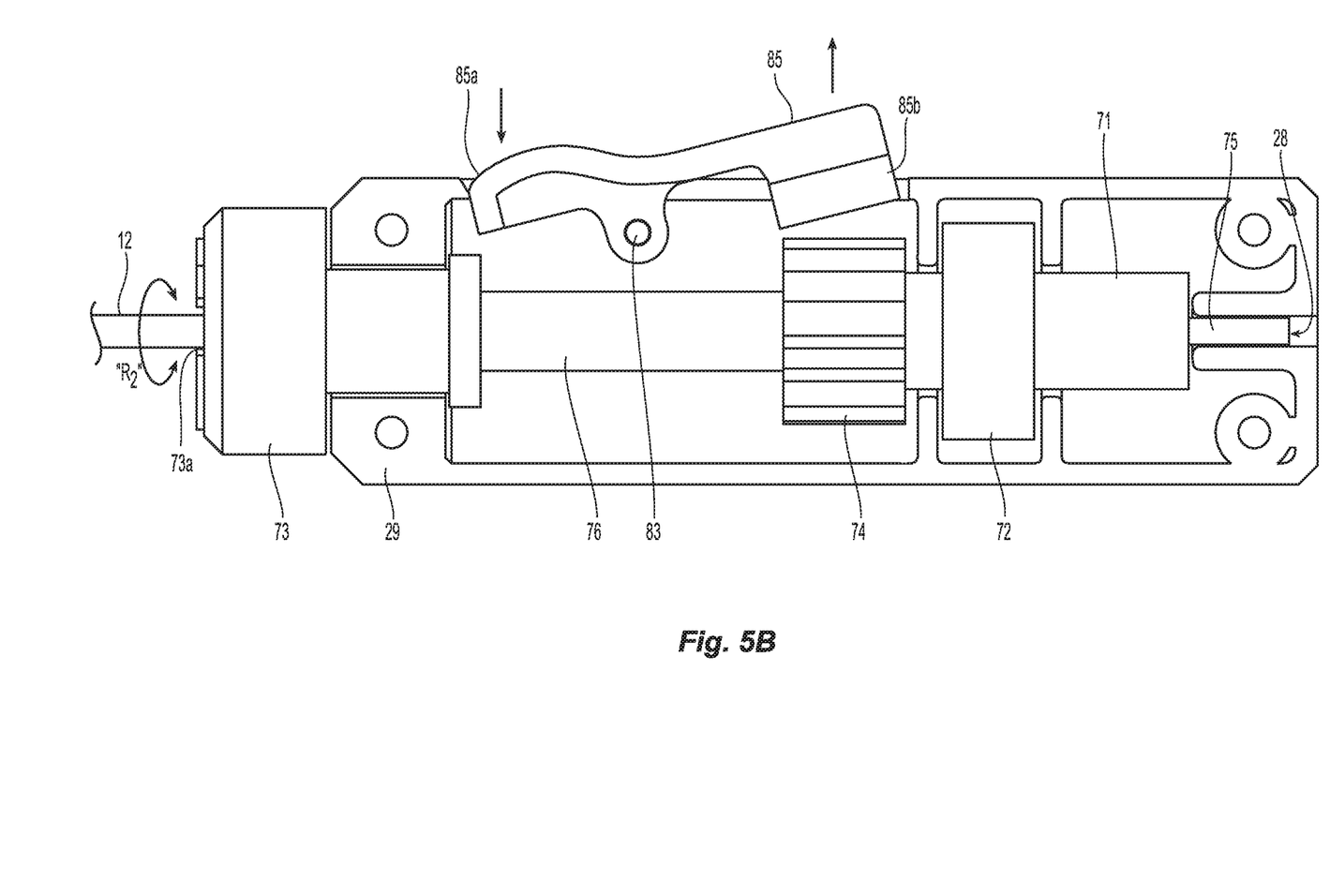
FIG. 5B is a side, interior view of tissue specimen bag furler activated.

The loading and unloading of the furler 10 are shown in FIGS. 5A and 5B. More particularly and as explained above, once the spindle assembly 70 is loaded and the housing halves 20a, 20b are assembled to form the housing 20, the distal end 73 of the spindle assembly 70 is rotated along in the direction of arrow "R1" while the activation switch 85 in the locked configuration. Gear 74 correspondingly rotates in the same direction "R1" and the proximal end of the activation switch pawls as the gear 74 rotates.

Mechanical interface 73a may also be a ratchet mechanism to facilitate loading the CFS 72. For example, as the ratchet-like mechanical interface 73a of distal end 73 is rotated in the direction "R1" (See FIG. 5A), gear 74 spins against the bias of CFS 72 spring 72 to load the CFS 72. When released at any point along rotation of the ratchet-like mechanical interface 73a, the proximal end 85b of the activation switch 85 pawls along the gear 74 and locks the gear 74 in place until the activation switch 85 is actuated. This ratchet-like mechanical interface 73a may facilitate the loading process.

Alternatively, the user may depress the distal end 85a of the activation switch 85 to pivot free the proximal end 85b of the activation switch 85 from the gear 74 while simultaneously turning the distal end 73 of the spindle assembly 70. Prior to releasing the distal end 73, the user would reengage the proximal end 85b of the activation switch 85 by releasing the distal end 85a of the activation switch 85.

Once loaded with the activation switch 85 in place preventing release of the gear 74, the user loads the bag 60 onto the dowel pin 68 as explained above and slides the bag 60 fully atop the shaft 12. When the bag 60 is properly positioned, the user actuates the activation switch 85 by depressing the distal end 85a of activation switch 85 into the housing 20 which, in turn, pivots the proximal end 85b of the activation switch 85 to disengage gear 74. This unloads the CFS 72 to cause rotation the shaft 12 in the direction "R2" (See FIG. 5B). Rotation of the shaft 12 correspondingly rotates the bag 60 causing the bag brim 65 to collapse and the bag 60 to furl around itself.

Once the bag 60 is completely furled, the dowel pin 68 may be released from the shaft 12 and the bag 60 (now in the furled configuration) may be easily inserted through an incision or natural opening into a surgical cavity or loaded atop a tissue specimen retrieval device (not shown). The user can then pre-load the furler 10 for another use using one of the mechanisms or techniques described above.

Figure 6:
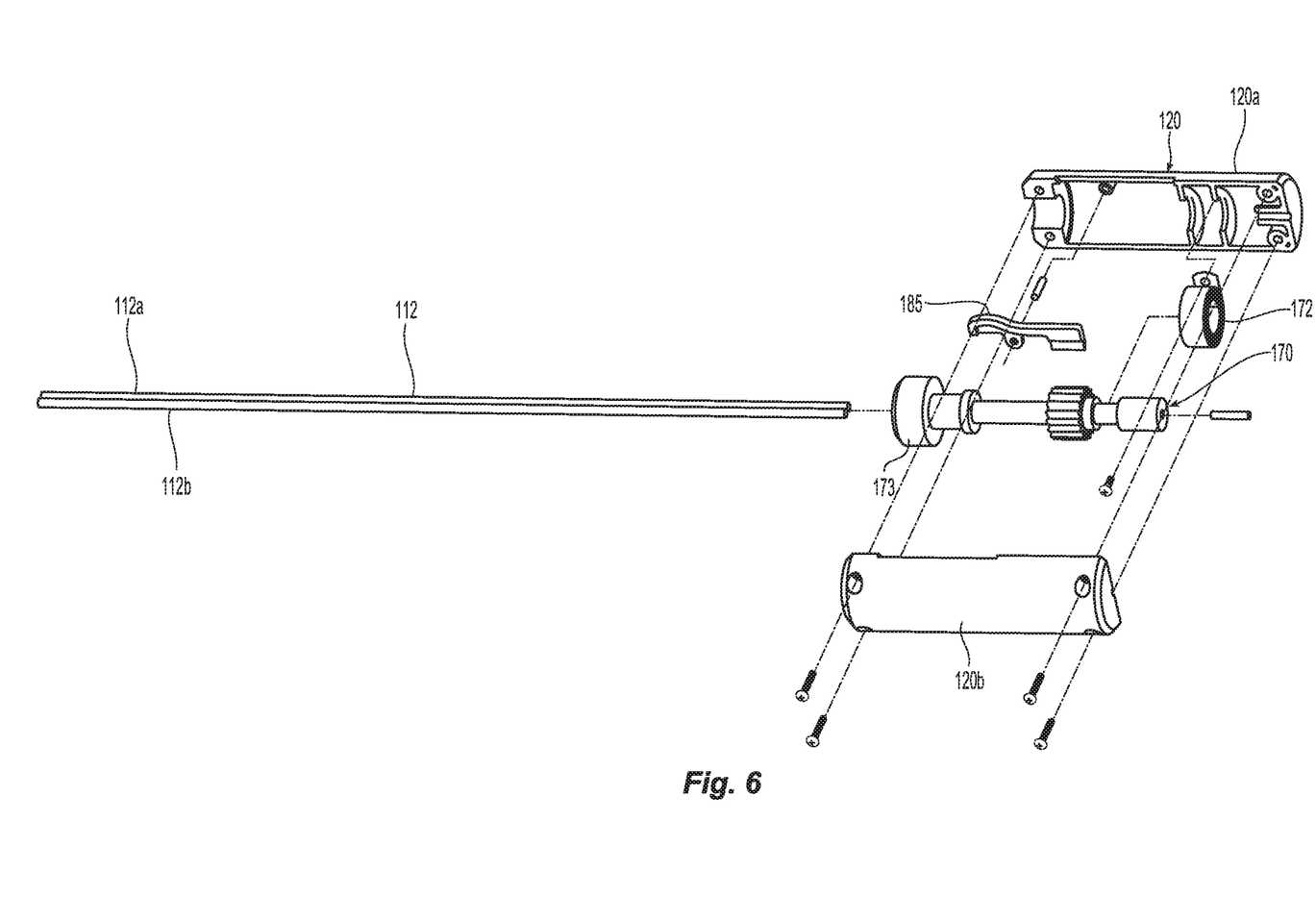
FIG. 6 is an exploded, perspective view of another embodiment of a tissue specimen bag furler.

FIG. 6 shows another embodiment of a furler 100 for use with a bag 60. Furler 100 is similar to furler 10 so only those features that are different will be described in detail herein. Furler 100 includes a similar housing 120 composed of mating halves 120a and 12b that encapsulate a spindle assembly 170. Spindle assembly cooperates with a CFS 172 to load and unload the furler 100 for use similar to furler 10 described above. Furler 100 includes an elongated shaft assembly 12 having elongated rods 112a and 112b that cooperate to furl bag 60. More particularly, in lieu of an elongated slot defined in the shaft (e.g., slot 17 defined in shaft 12 of furler 10) the two rods 112a, 112b cooperate to receive the dowel pin 68 of bag 60 therebetween and along a length thereof.

The present disclosure also relates to a method of furling a bag 60. More particularly and, in use, rotation of the distal end 173 of the spindle assembly 170 rotates the rods 112a, 112b in the direction "R1" and loads the spring 172. Similar to furler 10 above, the distal end 173 of furler 100 may also include a ratchet-type mechanism (not shown) to load the spring assembly 170.

Once the spring is loaded, the user then loads the dowel pin 68 between the rods 112a, 112b and slides the dowel pin 68 and bag 60 proximally such that the entire proximal end of the bag 60 is between the rods 112a, 112b. Switch 185 is then actuated causing the two rods 112a, 112b to rotate in the direction "R2" to collapse the bag brim 65 and furl the bag 60 around itself.

Once the bag 60 is completely furled, the dowel pin 68 may be released from between the rods 112a, 112b 12 and the bag 60 (now in the furled configuration) may be easily inserted through an incision or natural opening into a surgical cavity or loaded atop a tissue specimen retrieval device (not shown). The user can then pre-load the furler 100 for another use in the same fashion as described above.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A device for furling a tissue specimen retrieval bag, comprising:
   a housing supporting a spindle assembly therein, the spindle assembly including a drive shaft having a proximal end, a distal end, and a gear disposed therebetween;
   an activation switch pivotably coupled to the housing and configured for selective, operable engagement with the gear, the activation switch selectively positionable relative to the gear between a first position wherein the gear and drive shaft are locked from rotation in a first direction and a second position wherein the gear and drive shaft are free to rotate in the first direction;
   an elongated shaft operably coupled to the distal end of the drive shaft and configured for rotation therewith; and
   a biasing element configured to provide a rotational load to the drive shaft.

2. The device for furling a tissue specimen bag according to claim 1 wherein the biasing element is a constant force spring, a torsion spring, a compression spring, or an extension spring.

3. The device for furling a tissue specimen bag according to claim 1 wherein the biasing element is selectively loadable by rotating the distal end of the drive shaft in a second direction, opposite the first direction.

4. The device for furling a tissue specimen bag according to claim 3 wherein the activation switch includes a pawl-like proximal end that is configured to selectively engage the gear and allow rotation of the gear and drive shaft in the second direction and prevent rotation of the gear and drive shaft in the first direction.

5. The device for furling a tissue specimen bag according to claim 4 wherein the activation switch is biased in the first position to facilitate loading the drive shaft.

6. The device for furling a tissue specimen bag according to claim 1 wherein the distal end of the spindle assembly includes a ratchet-like mechanism to facilitate loading the drive shaft.

7. A device for furling a tissue specimen retrieval bag, comprising:
   a housing supporting a spindle assembly therein, the spindle assembly including a drive shaft having a proximal end, a distal end, and a gear disposed therebetween;
   an activation switch pivotably coupled to the housing and configured for selective, operable engagement with the gear, the activation switch selectively positionable relative to the gear between a first position wherein the gear and drive shaft are locked from rotation in a first direction and a second position wherein the gear and drive shaft are free to rotate in the first direction;
   an elongated shaft operably coupled to the distal end of the drive shaft and configured for rotation therewith, the elongated shaft including a slot defined therein and configured to operably engage a dowel pin associated with the tissue specimen bag for loading the tissue specimen bag atop the elongated shaft; and
   a biasing element configured to provide a rotational load to the drive shaft,
   wherein, once the dowel pin is operably engaged within the slot of the elongated shaft, actuation of the activation switch to the second position rotates the drive shaft and the elongated shaft to furl the tissue specimen bag about the elongated shaft.

8. The device for furling a tissue specimen bag according to claim 7 wherein the dowel pin slidingly engages the elongated shaft.

9. The device for furling a tissue specimen bag according to claim 7 wherein the biasing element is a constant force spring, a torsion spring, a compression spring, or an extension spring.

10. The device for furling a tissue specimen bag according to claim 7 wherein the biasing element is selectively loadable by rotating the distal end of the drive shaft in a second direction, opposite the first direction.

11. The device for furling a tissue specimen bag according to claim 10 wherein the activation switch includes a pawl-like proximal end that is configured to selectively engage the gear and allow rotation of the gear and drive shaft in the second direction and prevent rotation of the gear and drive shaft in the first direction.

12. The device for furling a tissue specimen bag according to claim 11 wherein the activation switch is biased in the first position to facilitate loading the drive shaft.

13. The device for furling a tissue specimen bag according to claim 7 wherein the distal end of the spindle assembly includes a ratchet-like mechanism to facilitate loading the drive shaft.

14. The device for furling a tissue specimen bag according to claim 7 wherein the dowel pin is welded, glued, molded or integrated onto an outer periphery of the tissue specimen bag.

15. A method of furling a tissue specimen bag, comprising:
   loading a tissue specimen bag onto an elongated shaft of a tissue furler, the tissue furler including:
   a housing supporting a spindle assembly therein, the spindle assembly including a drive shaft having a gear disposed therebetween, the elongated shaft operably coupled to a distal end of the drive shaft for rotation therewith;
   an activation switch pivotably coupled to the housing and configured for selective, operable engagement with the gear, the activation switch selectively positionable relative to the gear between a first position wherein the gear and drive shaft are locked from rotation in a first direction and a second position wherein the gear and drive shaft are free to rotate in the first direction;
   a biasing element configured to provide a rotational load to the drive shaft; and
   actuating the activation switch to rotate the drive shaft and the elongated shaft to furl the tissue specimen bag about the elongated shaft.

16. The method of furling a tissue specimen bag according to claim 15 wherein prior to loading the tissue specimen bag onto the elongated shaft, the method further includes rotating the distal end of the drive shaft in a second direction, opposite the first direction, to the load the biasing element.

* * * * *